United States Patent [19]

Ishige et al.

[11] Patent Number: 5,968,783
[45] Date of Patent: Oct. 19, 1999

[54] PROCESS FOR THE PREPARATION OF SUGAR NUCLEOTIDES

[75] Inventors: Kazuya Ishige, Hasakimachi; Kenji Takenouchi, Choshi, both of Japan

[73] Assignee: Yamasa Corporation, Chiba, Japan

[21] Appl. No.: 09/043,175

[22] PCT Filed: Jul. 10, 1997

[86] PCT No.: PCT/JP97/02387

§ 371 Date: Mar. 16, 1998

§ 102(e) Date: Mar. 16, 1998

[87] PCT Pub. No.: WO98/02566

PCT Pub. Date: Jan. 22, 1998

[30] Foreign Application Priority Data

Jul. 15, 1996 [JP] Japan ..................................... 8-204316

[51] Int. Cl.⁶ ............................ C12P 19/30; C12P 19/28; C12P 19/00; C12N 1/18
[52] U.S. Cl. ................................ 435/89; 435/85; 435/84; 435/72; 435/255.1; 435/171
[58] Field of Search ................................... 435/89, 85, 84, 435/72, 255.1, 171

[56] References Cited

PUBLICATIONS

Chemical Abstracts 84(7):41909f (1976).
Chemical Abstracts 72(7):41686h (1970).
Kawaguchi et al, Agric. Biol. Chem. 34(6):908–918 (1970).
Kimura et al, J. Bacteriol. 125(2):744–746 (1976).

*Primary Examiner*—Francisco Prats
*Attorney, Agent, or Firm*—Wenderoth, Lind & Ponack, L.L.P.

[57] ABSTRACT

The present invention relates to a process for preparing sugar nucleotides from nucleotides and sugar derivatives by the use of yeast, characterized in that the reactions are conducted at 20° C. or below. According to this process, even when the preparation is conducted on an enlarged scale, a reduction in the yield of a sugar nucleotide can be inhibited by a very simple means; lowering the reaction temperature 20° C. or below. Thus, the process is an extremely practical one applicable to the mass-production of sugar nucleotides.

5 Claims, 2 Drawing Sheets

PROCESS FOR THE PREPARATION OF SUGAR NUCLEOTIDES

This application is a 371 application of International Application No. PCT/JP97/02387 filed Jul. 10, 1997.

TECHNICAL FIELD

The present invention relates to a process for preparing sugar nucleotides, which are important substrates in the synthesis of sugar chains such as oligosaccharides.

BACKGROUND ART

Recent remarkable progress of sugar-chain science has clarified some of its physiological role, which makes it possible to develop pharmaceuticals and functional materials based on oligosaccharides possessing physiological activities. However, only limited types of oligosaccharides are currently available on the market, and in addition, they are extremely expensive. Moreover, those oligosaccharides can be produced only on a reagent level, and a mass-production method for them has not yet been fully established.

Conventionally, oligosaccharides have been produced by way of extraction from natural substances, chemical synthesis, enzymatic synthesis, or a combination of these. Among these processes, enzymatic synthesis has been considered the best suited for the mass-production for the following reasons: (1) enzymatic synthesis does not require intricate procedures such as protection and removal of protection, which are required for chemical synthesis, (2) substrate specificities of enzymes enable the synthesis of oligosaccharides having highly structural specificities. In addition, recent progress in recombinant DNA technology have made it possible to mass-produce various types of enzymes economically and in large quantities, which also contributes to establishing the superiority of enzymatic synthesis over other processes.

Two processes for the synthesis of oligosaccharides through use of enzymatic synthesis are available: a process that makes use of the reverse reaction of a hydrolase, and a process that makes use of a glycosyltransferase. The former has an advantage that it can employ inexpensive monosaccharides as the substrate, but as it employs the reverse reaction to the decomposition reaction, it is not necessarily the best process for the synthesis of oligosaccharides in terms of the yield and application to oligosaccharides possessing a complicated structure.

On the other hand, the latter makes use of a glycosyltransferase and has an advantage over the former in terms of the yield and application to the synthesis of oligosaccharides possessing a complicated structure. Moreover, the mass-production of various types of glycosyltransferase enabled by recent progress in recombinant DNA technology also contributes to realization of this process.

However, sugar nucleotides, which are sugar donors used in a synthesis that makes use of a glycosyltransferase, are with few exceptions still expensive, and are provided only in small amounts on reagent levels. There has been reported a process for preparing uridine diphosphate-N-acetylglucosamine (UDPAG), which is a donor of N-acetyl glucosamine, by use of an osmolarity-resistant yeast (Japanese Patent Application Laid-Open (kokai) No. 8-23993), but problems still remain to be solved before its industrial production is realized.

DISCLOSURE OF THE INVENTION

The inventors of the present invention have carried out studies on a process for preparing UDPAG by use of yeast for an enzyme source reported by Tochikura et al., wherein uridylic acid and glucosamine are used as the substrates (Japanese Patent Publication (kokoku) No. 49-8278: Tochikura's method), and have confirmed that although Tochikura's method enables high yield production of UDPAG in small scale production, synthesis efficiency lowers considerably when the reaction scale is enlarged (for example, to a reaction scale of greater than dozens of milliliters).

On the basis of the above, the present inventors have carried out earnest studies in an attempt to develop a practical process for the production of sugar nucleotides which makes it possible to enlarge the reaction scale without reducing the production yield, and have confirmed the following points: (1) the synthesis of UDPAG by use of yeast is generally divided into two groups of reactions: a group of reactions relating to the production and accumulation of uridine triphosphate which couples to the production of adenosine triphosphate by the respiratory system, and another group of reactions which pertain to the synthesis of the sugar moiety of UDPAG, for example, phosphorylation and acetylation of glucosamine; (2) in Tochikura's method, there is a time lag at the beginning of the synthetic reaction of UTP and the beginning of the synthesis of the sugar moiety. Enlargement of reaction scale makes the time lag extended, resulting in a reduction in the production yield of synthesized UDPAG; (3) when the reactions are conducted at temperatures of not higher than approximately 20° C.—which temperature condition is quite an unexpected one in consideration of the optimal temperature of the enzyme of yeast—the synthetic reaction of UTP and that of the sugar moiety are well-balanced, to thereby enable an efficient synthesis of UDPAG on a greater reaction scale; and (4) this approach is applicable not only to UDPAG but also to other sugar nucleotides as well. The present invention was accomplished based on these findings.

Accordingly, the present invention is directed to a process for preparing sugar nucleotides from nucleotides and sugar derivatives by the use of yeast, wherein the reactions are conducted at about 20° C. or below.

BEST MODE FOR CARRYING OUT THE INVENTION

Figure 1:
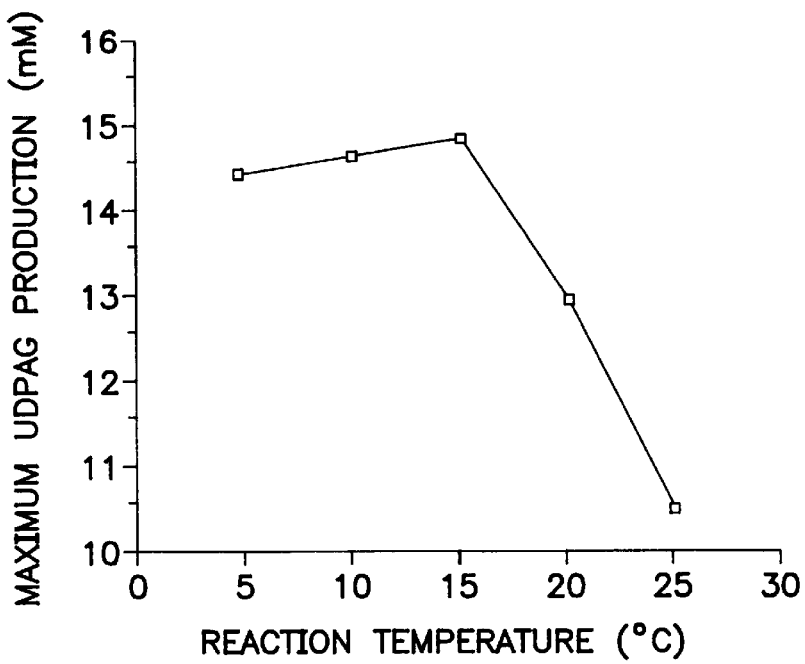
FIG. 1 is a graph showing the effect of reaction temperature on the production yield of UDPAG.

The sugar nucleotides, which are the target substances of the present invention, are not particularly limited so long as they are known sugar nucleotides. Specific examples include UDP sugars such as UDPG, UDPAG, UDP galactose, and UDP glucuronic acid; GDP sugars such as guanosine diphosphate mannose (GDP mannose), GDP fucose, and GDP glucose; ADP sugars such as adenosine diphosphate glucose (ADP glucose); dTDP sugars such as thymidine diphosphate glucose (dTDP glucose) and dTDP galactose; and CDP sugars such as cytidine diphosphate glucose (CDP glucose). Also, examples of sugar moieties of the sugar nucleotides include deoxy sugar, amino sugar, uronic acid, or sugar alcohol, in addition to monosaccharides.

The process of the present invention is used to produce the target substances, sugar nucleotides, from nucleotides and sugar derivatives by use of yeast.

A variety of types of yeast may be used without any particular limitation so long as they have hitherto been employed in conventional processes, for example, Tochikura's method, for the production of sugar nucleotides such as UDPAG. Specifically, there may be used different types of yeast such as those which belong to the genus Sacchromyces, genus Zygosaccharomyces, genus Candida, genus Torulopsls, genus Hansenula, genus Debaryomyces, etc. Although either viable or dry yeast may be used, dry yeast is more preferred from the point of reaction yield.

The nucleotides and sugar derivatives subjected to the reactions may be suitably selected in accordance with the type of the sugar nucleotide of interest. Specifically, when the sugar nucleotide is a UDP sugar, the nucleotide is uridine monophosphate (UMP), and the sugar derivative is suitably selected in accordance with the sugar nucleotide of interest, from among glucose, glucosamine, galactose, glucuronic acid, etc. Similarly, in the case of a GDP sugar, the nucleotide is guanosine monophosphate (GMP), and the sugar derivative is suitably selected in accordance with the sugar nucleotide of interest, from among mannose, fucose, glucose, etc.; and in the case of an ADP sugar, dTDP sugar, or CDP sugar, the nucleotide is adenosine monophosphate (AMP), thymidine monophosphate (dTMP), or cytidine monophosphate (CMP), and the sugar derivative is suitably selected in accordance with the sugar nucleotide of interest, from among glucose, galactose, etc.

These nucleotides and sugar derivatives which are usable in the reactions are available on the market, and thus, commercial products may be used. The concentration of respective materials is suitably determined within the range of about 1 to about 50 mM, preferably about 10 to about 30 mM.

In addition to the above-described nucleotides and sugar derivatives, inorganic phosphoric acids and energy sources are preferably added to the reaction system, to thereby perform the process of the present invention.

Useful inorganic phosphoric acids include potassium phosphate, which may be used either as is or, preferably, in the form of a phosphate buffer. The concentration of the inorganic phosphoric acid during use is suitably determined within the range of about 10 to about 500 mM, preferably about 100 to about 300 mM. Also, the pH of the phosphate buffer is determined within the range of about 6 to about 8.

Examples of available energy sources include sugars such as glucose and fructose; and organic acids such as acetic acid and citric acid. Sugars used as energy sources may also serve as the above-mentioned sugar derivatives.

The reactions comprise the following steps. Yeast, nucleotide, and a sugar derivative are added to phosphate buffer. Energy sources may also be added as needed. The mixture is allowed to react at a temperature of not higher than approximately 20° C., preferably about 5° C. to about 20° C., more preferably about 10° C. to about 20° C., for about 2 hours to about 50 hours with stirring as needed.

The thus-obtained sugar nucleotide may be isolated and purified by customary isolation and purification means (ion exchange chromatography, adsorption chromatography, salting out, etc.) employed for sugar nucleotides.

EXAMPLES

The present invention will next be described in detail by way of examples, which should not be construed as limiting the invention. In the examples, sugar nucleotides contained in the reaction mixture were quantitatively determined by HPLC, wherein an ODS-AQ 312 column made by YMC was used for separation, and 0.5 M potassium dihydrogenphosphate solution was used as an eluent.

Example 1

Synthesis of UDPAG (1)

A reaction mixture (80 ml) of 20 mM 5'-UMP, 20 mM glucosamine, 100 mM glucose, 200 mM phosphate buffer (pH 8.0), and 10 mM $MgCl_2$ was placed in a 100-ml beaker. Dry baker's yeast (24 g, Oriental Yeast Industries K.K.) was suspended in the reaction mixture. Reaction was allowed to proceed with stirring up to 50 hours at a reaction temperature of 5° C., 10° C., 15° C., 20° C., or 25° C. The maximum production yield of UDPAG was determined. The production of UDPAG was quantitatively determined by subjecting the supernatant of the reaction mixture obtained by centrifugal separation to an analysis by high performance liquid chromatography (HPLC).

The results are shown in FIG. 1. As is apparent from FIG. 1, it was possible to produce 13 mM or more of UDPAG at a temperature of 20° C. or less, preferably 5–20° C., proving that the reaction temperature unexpectedly affected the production yield of UDPAG. Incidentally, when the reaction was performed at 15° C., production of 14.5 mM UDPAG was confirmed at the end of 48 hours of reaction.

Example 2

Synthesis of UDPAG (2)

A reaction mixture (80 ml) of 20 mM 5'-UMP, 20 mM glucosamine, 100 mM glucose, 200 mM phosphate buffer (pH 8.0), and 10 MM $MgCl_2$ was placed in a 100-ml beaker. Dry baker's yeast (24 g, Oriental Yeast Industries K.K.) was suspended in the reaction mixture. Reaction was allowed to proceed with stirring at the reaction temperature of 28° C. (the reaction temperature used in Tochikura's method) or 15° C. (a reaction temperature of the present invention). The production yield of UDPAG was chronologically determined. The UDPAG production was quantitatively determined by subjecting the supernatant obtained by centrifugal separation of the reaction mixture to an analysis by high performance liquid chromatography (HPLC).

Figure 2:
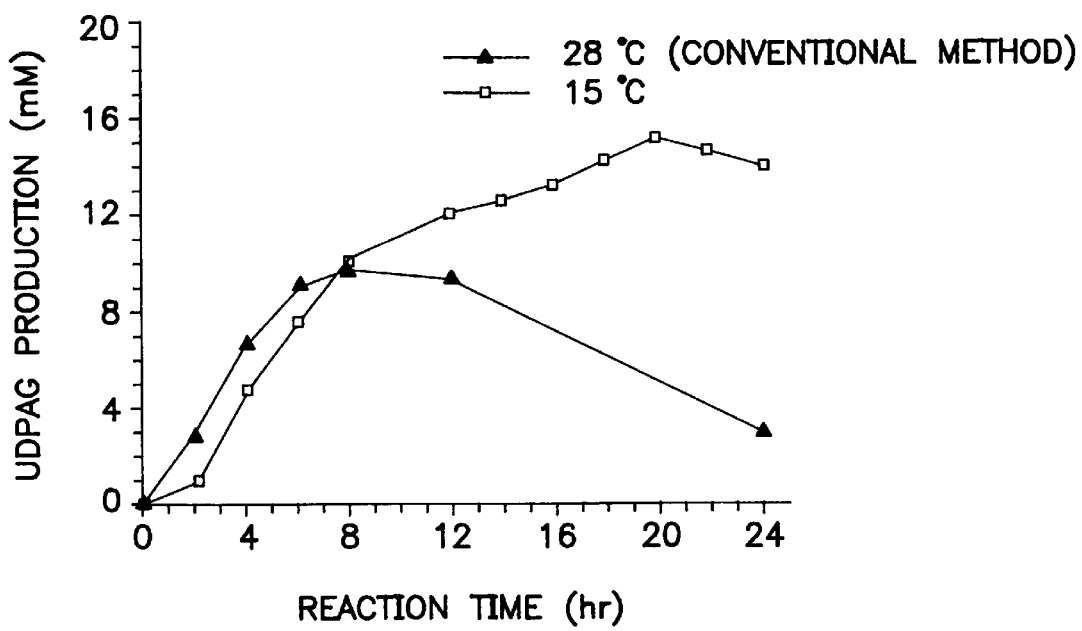
FIG. 2 is a graph showing chronological changes of the production yield of UDPAG on a reaction scale of 80 ml.

The results are shown in FIG. 2. As is apparent from FIG. 2, when the reaction temperature was 28° C., the production yield reached its maximum, 9.5 mM, eight (8) hours after start of the reaction, and subsequently, the production yield of UDPAG reduced rapidly. In contrast, when the reaction temperature was 15° C., the production yield reached its maximum, 15 mM, twenty (20) hours after the start of reaction, and the reduction in the amount of UDPAG was very small even twenty-four (24) hours after the start of reaction.

Example 3

Synthesis of UDPAG (3)

A reaction mixture (1,000 liters) having a composition similar to that used in Example 1 was placed in a 2,000-L tank. Dry baker's yeast (300 Kg) was suspended in the reaction mixture, and reaction was allowed to proceed with stirring at 28° C. (Tochikura's method) or 15° C. (present invention), so as to prepare UDPAG.

Figure 3:
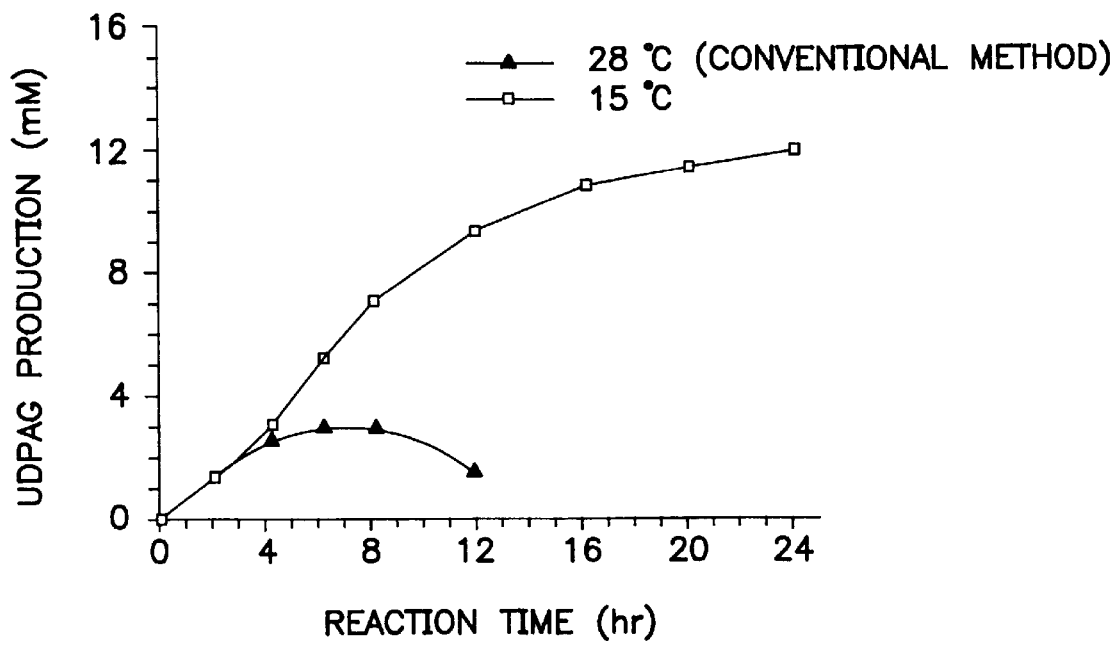
FIG. 3 is a graph showing chronological changes of the production yield of UDPAG on a reaction scale of 1,000 ml.

The results are shown in FIG. 3. As is apparent from FIG. 3, when the reaction temperature was 28° C., the amount of UDPAG synthesized was 3 mM at most. However, dropping of the reaction temperature alone enabled synthesis of approximately 12 mM UDPAG. Although this production yield was somewhat smaller than that achieved in the case of the 80-ml scale production in Example 1, the process of the present invention was proven to be practical in view that the reduction in production yield was suppressed to a small extent.

In this connection, when the process was applied to an even greater scale reaction of several thousand liters, preparation of sugar nucleotides on a Kg level was confirmed.

Example 4
Synthesis of UDPG

Into a reaction mixture (5 ml) having a composition of 40 mM UMP, 400 mM glucose, 200 mM sodium phosphate (pH 8.0), and 10 mM $MgCl_2$ was suspended dry baker's yeast (0.5 g, Oriental Yeast Industries K.K.). Reaction was allowed to proceed with stirring at a reaction temperature of 20° C., 23° C., or 28° C. The production yield of UDPG was chronologically determined.

Figure 4:
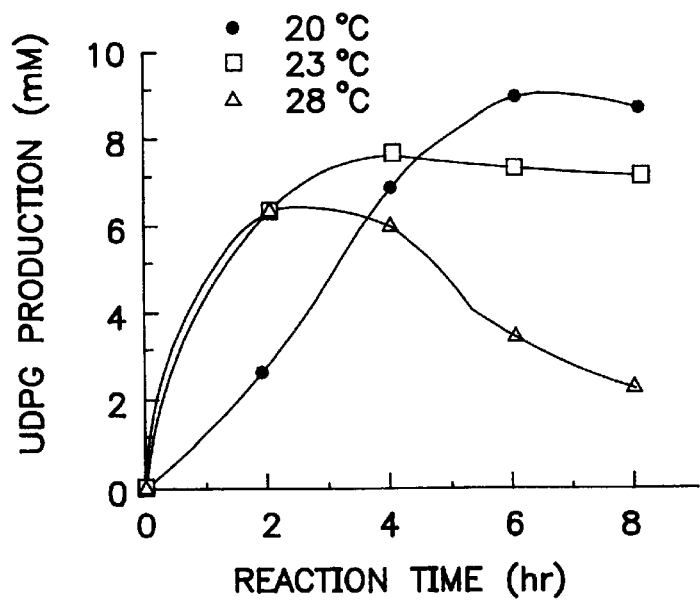
FIG. 4 is a graph showing the effect of reaction temperature on the production yield of uridine diphosphate glucose (UDPG).

The results are shown in FIG. 4. As is apparent from FIG. 4, it was confirmed that although the higher the temperature, the faster the synthesis rate, the ultimate yield was highest at 20° C., approximately 8 mM UDPG.

Example 5
Synthesis of GDP mannose

A reaction mixture (20 ml) having a composition of 40 mM GMP, 200 mM mannose, 200 mM potassium phosphate (pH 8.0), and 10 mM $MgCl_2$ was placed in a 100-ml beaker. Dry baker's yeast (2 g, Oriental Yeast Industries K.K.) was suspended in the reaction mixture. Reaction was allowed to proceed with stirring at a reaction temperature of 20° C. for seven hours. After completion of reaction, the reaction mixture was processed at 100° C. for five minutes, and cells of the yeast were removed by centrifugal separation (2,000× g; 10 minutes). When the recovered supernatant was subjected to HPLC analysis, a yield of 11.2 mM GDP mannose was confirmed.

INDUSTRIAL APPLICABILITY

By a very simple approach of reducing the reaction temperature to approximately 20° C. or lower, the present invention enables inhibition of reduction in yield of the synthesis of sugar nucleotides even when the reaction scale is enlarged, and thus the invention process has been proven to be a very practical method that opens the way to mass-production of sugar nucleotides.

We claim:

1. A process for preparing a sugar nucleotide selected from the group consisting of UDP sugars and GDP sugars, which comprises reacting a nucleotide and a sugar derivative in the presence of yeast at a temperature not higher than approximately 20° C. for more than 4 hours.

2. The process according to claim 1, which is performed at a temperature of about 5° C. to about 20° C.

3. The process according to claim 1, which is performed at a temperature of about 10° C. to about 20° C.

4. The process according to claim 1, which is performed in the presence of an inorganic phosphoric acid.

5. The process according to claim 1, wherein the sugar nucleotide is selected from the group consisting of UDP-N-acetylglucosamine, UDP glucose, UDP galactose, UDP glucuronic acid, GDP mannose, GDP fucose and GDP glucose.

* * * * *